April 15, 1975 S. R. NEMCIK Plant Pat. 3,703
AVOCADO TREE
Filed March 12, 1974
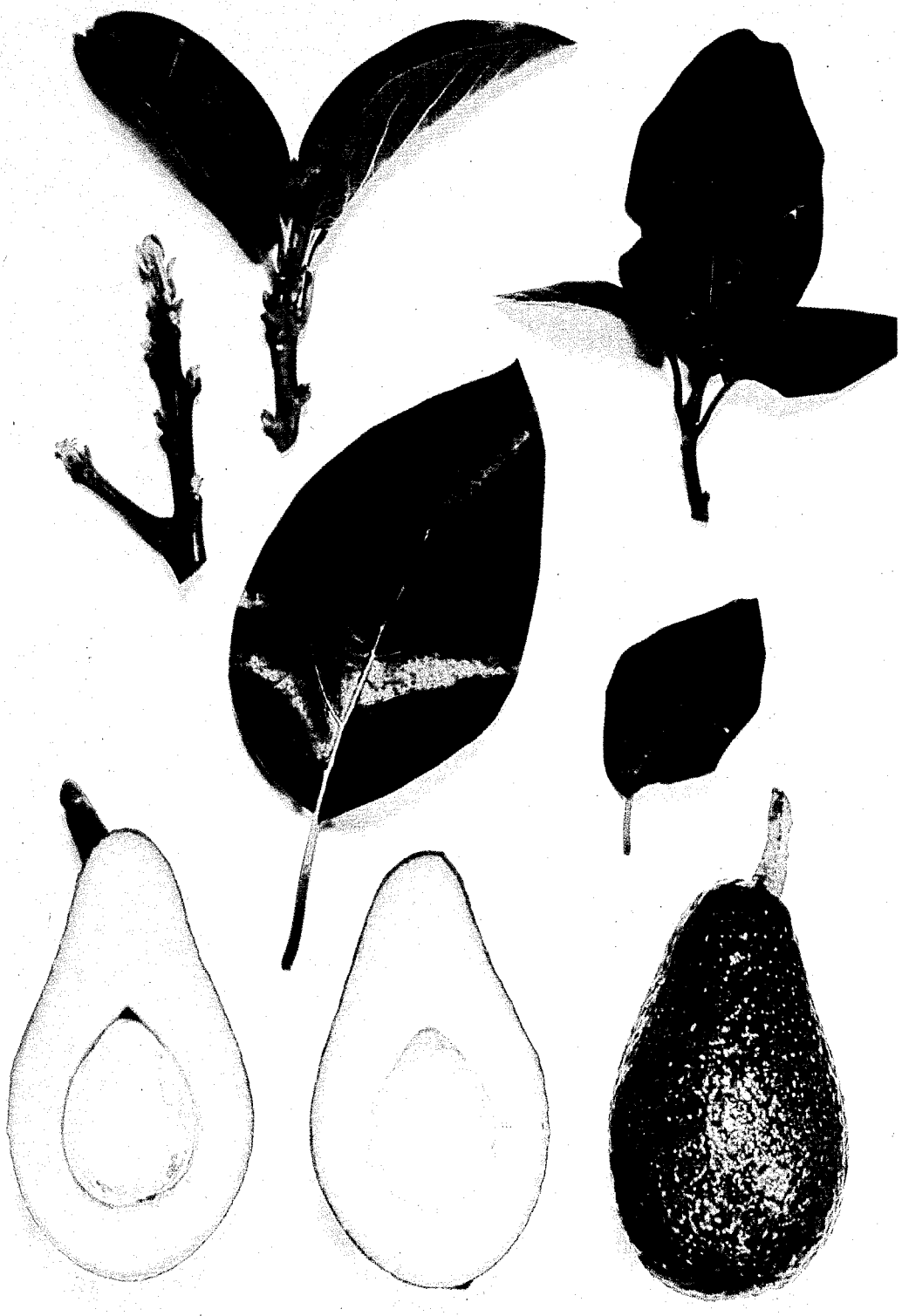

United States Patent

Plant Pat. 3,703

Patented Apr. 15, 1975

3,703

AVOCADO TREE

Stephen R. Nemcik, Buena Park, Calif., assignor of a fractional part interest to Frank Gilkerson Filed Mar. 12, 1974, Ser. No. 450,480

Int. Cl. A01h 5/03

U.S. Cl. Plt.—44 1 Claim

ABSTRACT OF THE DISCLOSURE

A new variety of avocado tree, grown as a seedling from the seed of the (unpatented) Zutano variety. This new variety is distinctive in that the fruit matures (reaches 8% in oil content) in late September or early October, exceptionally early maturing for a fall-fruiting type, and from three to four weeks earlier than such commercial fall varieties as Zutano and Bacon. The new variety produces fruit which is more uniform in size and larger than fruit from the Bacon and Zutano, the fall-fruiting varieties. In addition to a seed size smaller than is common to other fall varieties, the flesh of this fruit is smooth-textured, has a rich, nutty flavor, and no perceptible fiber. The tree is resistant to frost.

This invention relates to an avocado tree grown from seed in the inventor's orchard in Buena Park, Orange County, Calif. The characteristics hereafter described will be such as have been observed in trees grown in that geographical region. When the new seedling had grown long enough to show indications of promise, it was asexually reproduced by means of budwood, grafted onto Fuerte and Topa understocks. The asexually reproduced trees set a few fruit which matured the first year after grafting. The characteristics of the new variety are reproduced in stock similarly grafted.

This new variety is shown to have been precocious and a bearer of heavy to moderately heavy crops, and has indicated frost resistance with no damage to foliage at sustained low temperatures between 27 and 28 F. and temperatures between 24 and 25 for a duration of three hours or longer.

"Maturity," as herein used, refers to the legal standard set by the State of California, namely when the oil content of an avocado reaches 8%. Oil content of this new fruit reaches 8% to 12% in late September or early October, increasing gradually to 16% to 22% in February, the nominal end of the season for this fruit at Buena Park, Calif. The time when the bloom first sets fruit until the time of earliest maturity is approximately six months. The mature fruit holds well on the tree for an additional three to four months.

Fruit of this new variety may be described as ranging from medium to large with diameters of from 2¾" to 3½" and lengths ranging from 4¾" to 6¼". Fruit weight varies from 8 oz. to 12 oz. at early maturity and from 9 oz. to 16 oz. with the advance of the season.

The fruit, more uniform in size than is common with other fall varieties (i.e., Zutano, Bacon) is elongated pear shaped with the blossom end broadly rounded with occasional variations. Stems vary from 2½" to 4" in length and are of medium caliper. Fruit holds well on the stem and is not subject to drop.

The skin of the fruit is smooth, leathery and of medium thickness. It has yellowish to light green stomata, distributed fairly uniformly over the fruit with some concentration of stomata toward the base. Overall, the skin has a bright, glossy appearance. Color hues may vary from lighter to darker green with variations in season and districts where grown.

The flesh of the fruit varies from light green adjacent to the skin to a creamy yellow adjacent to the seed cavity. Its texture is smooth and fine, without discernible fibers. It softens uniformly, and has a nutty flavor ranging in eating quality from good to excellent.

The new variety differs from the Zutano in several respects, in addition to the fact that it matures earlier and bears larger fruit than that produced by the Zutano. Crushed leaves of this new variety have no readily detactable anise odor common to such fall varieties as Zutano and Bacon. Soft terminal wood does not exhibit the pronounced reddish-brown flecking common to such fall varieties as Zutano and Bacon. A small detectable spur is centered or slightly offset in the concave indentation at the blossom end of the fruit of this new variety, whereas this spur does not occur on the Zutano variety. The fruits average from three to six ounces heavier than those of Zutano or Bacon.

The new variety preserves its characteristics when propagated by grafting.

The accompanying drawings illustrate the terminal structure of the fruit-bearing twigs, and show the new leaf and the mature leaf. They also show the external appearance of the fruit and opposite halves of a fruit which has been cut in half lengthwise and laid open to reveal the appearance of the flesh, of the seed, and of the seed cavity.

As to color effect, color names used herein with initial capital letters indicate values taken from the Nickerson Color Fan, put out by Munsell Color Co. Colors named without initial capital letters are used where the common name is sufficiently definite to avoid the need for greater precision.

THE TREE

The original seedling has grown to twenty-one feet in height, spreading at the top to about ten feet. The growth is vigorous and upright, with the foliage moderately dense. The tree is productive and a regular bearer. It has a medium slender trunk, measuring about 10½" at five feet above the ground. The bark is medium smooth, and the branches are medium slender.

The soft terminal wood on the branches is Strong Yellow Green, 5GY6/8, varying to Dark Yellow Green, 10GY4/5. Its coloration is distinctive in that it does not exhibit reddish-brown flecking, such as is common to the Fuerte avocado, and such fall varieties as Zutano and Bacon. The primary wood, particularly the secondary bark generally, is Moderate Yellow Green, 2.5GY5/5. Seasonally this new variety may exhibit a minimal amount of darker green flecking on the terminal growth.

The hardwood bark is evenly lenticeled. These lenticels are of average quantity and range from medium to small in size.

The overall appearance of the mature bark is clean and regular, and not distinctly different from that of many other avocado varieties.

FOLIAGE

Leaves range from medium to large in size, being from 2¼" to 8" in length, and 1½" to 4¼" in width. They are ovate in form, with acute tip, varying to elliptic, and are of medium thickness.

The color of the leaves on the upper side of the new growth is Moderate Yellow Green, 5GY5/6, with pronounced reddish-bronze overcast. On the under side, the new leaves show Moderate Yellow Green, 5GY5/6, varying to Strong Yellow Green, 5GY6/8, with bronze undertone.

In the mature leaf, the coloration on the upper side is a semi-glossy Grayish Olive Green, 7.5GY3/2, varying to lighter yellow green with changes in season and differences in soil. The under side of the mature leaf (not shown) is dull, varying from Strong Yellow Green, 7.5GY6/8, to Moderate Olive Green, 5GY4/3.

The veining of the leaves is generally quite pronounced, being Strong Yellow Green, 2.5GY6/8, to Strong Greenish Yellow, 10Y/9, in color. The leaf margins are regular in form and very slightly wavy, the leaves being both opposite and alternate.

The petiole is of medium length and medium caliper.

The tree begins to flower early in February, and its blooming season ends in mid-May. This is earlier than most varieties, but comparable with the blooming season for Zutano.

FRUIT

The tree sets fruit beginning in late February and extending through April. The fruit matures at the earliest in late September, or early October, reaching 12% to 14% or more in oil content in the month of November. In short, the new variety generally matures three to four weeks earlier than other commercial fall varieties in the same geographical area.

The fruit is elongated pear shape, with moderately slender neck with some variation, and skin which is of medium thickness and leathery, and which peels readily from the flesh of the ripe fruit. The stem is of average thickness, strong, and from 2½" to 4" in length. The stem is offset on the fruit, and most fruit of this variety is slightly curved-in opposite the stem, there being a detectable elongated indentation at the neck of the fruit of from 1¾" to 1". The blossom end is full, and offset from the base or blossom end is a slight circular identation of varying size, from ⅜" to ⅝". As noted previously, a detectable small spur, which does not occur on the Zutano variety, is centered and slightly offset in the concave indentation at the blossom end of the fruit.

The skin generally is bright, glossy, and Dark Yellowish Green, 2.5G3/3, with variations of lighter to darker green in different soils and seasons. A slightly raised stomata, which is from Strong Yellow Green, 2.5GY7/10, to Strong Yellow Green, 2.5GY6/8, is distributed over the surface of the skin, being somewhat concentrated at the blossom end. A very slight russeting occurs on the bottom third of the fruit with advanced maturity, at Buena Park, Calif.

The flesh is smooth and fine, with no discernible fiber. It is thick between skin and seed cavity, and its color varies irregularly from near Pale Orange Yellow, 7.5YR9/4, being a Brilliant Yellow Green, 2.5GY9/8, adjacent to the seed, and becoming Moderate Yellow Green, 5GY5/6, adjacent to the outer skin. The flesh maintains its natural color well, after exposure to air, and softens evenly and smoothly when ripe. It has a nutty flavor, varying from good to excellent, reaching its peak flavor at an oil content of 10% or slightly more.

The seed cavity is from 2" to 2½" in length, and from 1¼" to 1½" in width, with a seed coat which adheres to the seed rather than to the flesh.

The seed is from small to medium, being 1⅞" in length and 1¼" in width. It is ovate, and slightly offset at the base. There are no unusual convolutions. The seed has a waxy surface, typical of the avocado seed, and is near Pale Orange Yellow, 7.5YR9/4, in color, varying to a lighter, more neutral coloring, in relation to maturity.

Due to the somewhat tough, leathery texture of the skin, the shipping and keeping quality of this variety is superior.

Foliage of this variety will withstand frost, without damage, for a long interval at 28° F., for about six hours at a temperature of 27° F., and for three hours at a temperature of 25° F. or less.

I claim:

1. The new variety of avocado tree substantially as shown and described herein, being distinguished for its ability to produce fruit with a seed of unusually small size in relation to fruit size and fruit flesh and to bring this fruit to maturity several weeks earlier than the fruit of comparable fall-maturing avocado varieties in the same growing area; the fruit of this variety also being notable because of its smooth, leathery skin which enhances the resistance of the fruit to damage in shipping and handling; said variety further bearing fruit the interior flesh of which retains its natural color after exposure to air.

No references cited.

ROBERT E. BAGWILL, Primary Examiner